United States Patent [19]

Grisar et al.

[11] Patent Number: 4,734,422
[45] Date of Patent: Mar. 29, 1988

[54] CARDIOTONIC AROYLTHIAZOLONES AND THE USE THEREOF

[75] Inventors: J. Martin Grisar, Wissembourg, France; Richard C. Dage; Richard A. Schnettler, both of Cincinnati, Ohio

[73] Assignee: Merrell Dow Pharmaceuticals Inc., Cincinnati, Ohio

[21] Appl. No.: 21,538

[22] Filed: Feb. 26, 1987

Related U.S. Application Data

[63] Continuation of Ser. No. 786,984, Oct. 15, 1985, abandoned.

[51] Int. Cl.⁴ ............................................ A61K 31/425
[52] U.S. Cl. .................................................... 514/369
[58] Field of Search ......................... 514/369; 548/188

[56] References Cited

U.S. PATENT DOCUMENTS 4,418,070 11/1983 Okonogi et al. .................... 514/369
4,623,651 11/1986 Grisar ................................... 514/342
4,649,146 3/1987 Takaya et al. ....................... 514/307
4,670,450 6/1987 Schnettler et al. ................. 514/341

FOREIGN PATENT DOCUMENTS 64657 11/1982 European Pat. Off. ............ 514/369
200402 5/1983 Fed. Rep. of Germany ...... 514/369

OTHER PUBLICATIONS

Chem. Abst. 84: 135629(s)(1976)–Manghisi et al.
U.S. Ser. No. 787,276, filed 10-15-85.
U.S. Ser. No. 787,226, filed 10-15-85.
U.S. Ser. No. 797,579, filed 11-13-85.

Primary Examiner—Douglas W. Robinson
Attorney, Agent, or Firm—Stephen L. Nesbitt

[57] ABSTRACT

Aroylthiazolones enhance myocardial contractile force and are useful as cardiotonics in the treatment of heart failure.

18 Claims, No Drawings

CARDIOTONIC AROYLTHIAZOLONES AND THE USE THEREOF

CROSS-REFERENCE TO RELATED APPLICATION

This is a continuation of application Ser. No. 786,984, filed Oct. 15, 1985, now abandoned.

BACKGROUND OF THE INVENTION

This invention relates to the ability of certain aroylthiazolones to enhance myocardial contractile force and the use of these compounds as cardiotonics in the treatment of heart failure.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and high-output and low-output heart failure. Heart failure can be caused by myocardial ischemia, myocardial infarction, excessive alcohol usage, pulmonary embolism infection, anemia, arrhythmias and systemic hypertension. Symptoms include tachycardia, fatique with exertion, dyspnea, orthopnea and pulmonary edema.

Treatment involves either removal or correction of the underlying cause or control of the heart failure state. Management or control can be accomplished by increasing cardiac output or by decreasing cardiac workload. While workload can be reduced by reduction of physical activities and by physical and emotional rest, increasing cardiac output has traditionally involved digitalis therapy. Digitalis stimulates contractile force of the heart which increases cardiac output and improves ventricular emptying. In this way, digitalis therapy normalizes venous pressure and reduces peripheral vasoconstriction, circulatory congestion and organ hypoperfusion.

Unfortunately, optimal doses of digitalis vary with the patient's age, size and condition and the therapeutic-to-toxic ratio is quite narrow. In most patients the lethal dose is only about five to ten times the minimal effective dose with toxic effects becoming apparent at only 1.5-2 times the effective dose. For these reasons, dose must be carefully tailored to suit the individual and frequent clinical examination and electrocardiogram is necessary to detect early signs of digitalis intoxication. Nevertheless digitalis intoxication is reported in up to one-fifth of hospitalized patients undergoing therapy. The need for less toxic cardiotonic agents is thus readily apparent.

Applicants have discovered that certain aroylthiazolones possess patent cardiotonic activity and by comparison to digitalis have fewer toxic effects.

SUMMARY OF THE INVENTION

This invention is directed to pharmaceutically active aroylthiazolones of formula 1

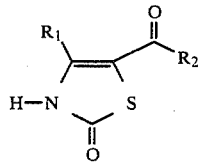

wherein
$R_1$ is a hydrogen or $(C_1-C_4)$alkyl group; and
$R_2$ is a phenyl or benzyl group either optionally substituted with one or two members of the group consisting of $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, trifluoromethyl, cyano, amino, mono and di $(C_1-C_4)$alkylamino, pyrrolidino, piperidino, morpholino, piperazino and N-$(C_1-C_4)$alkyl-piperazino and halogen or with a methylenedioxy group.

These compounds enhance myocardial contractile force and are useful as cardiotonics in the treatment of heart failure.

DETAILED DESCRIPTION OF THE INVENTION

The formula 1 compounds exists in two tautomeric forms structurally depicted in formula 2

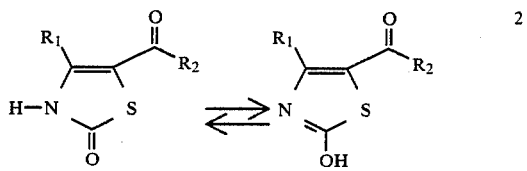

wherein $R_1$ and $R_2$ are as defined above. Throughout this disclosure, aroylthiazolones of formula 1 are intended to include both tautomers of formula 2.

The ring nitrogen atom of the fomula 1 compounds can be substituted with a $(C_1-C_4)$alkyl group, an alkanoyl group such as an acetyl group, or a benzoyl group. These nitrogen substituted compounds are equivalent to the unsubstituted compounds primarily because the substituent is cleved upon administration to a patient but also because many of the nitrogen substituted compounds independently possess significant ability to enhance myocardial contractile force and are useful cardiotonic agents.

As used herein the term $(C_1-C_4)$alkyl and the alkyl portion of the alkoxy, alkylthio, alkylsulfinyl, alkylsulfonyl, mono- and di-alkylamino, and N-alkylpiperazino groups means a straight or branched alkyl group of from one to four carbon atoms. Illustrative examples of a $(C_1-C_4)$alkyl group are methyl, ethyl, isopropyl, butyl, and sec-butyl. The term halogen means a fluoro, chloro, bromo or iodo group.

Preferred compounds of this invention are those compounds of formula 1 wherein $R_1$ is a hydrogen, methyl, or ethyl group. Also preferred are those formula 1 compounds wherein $R_2$ is an optionally substituted phenyl group. More preferred are those compounds of formula 1 wherein $R_2$ is a phenyl optionally substituted with an amino or a mono- or di-$(C_1-C_4)$alkylamino group. The most preferred compounds of this invention are those compounds of formula 1 wherein $R_2$ is a dimethylaminophenyl group and those compounds wherein $R_1$ is methyl group.

As examples of compounds of formula 1 there can be mentioned the following:
5-(4-cyanobenzoyl)-4-methyl-2(3H)-thiazolone;
5-benzoyl-4-methyl-2(3H)-thiazolone;
4-methyl-5-(4-fluorobenzoyl)-2(3H)-thiazolone;
5-(3-chlorobenzoyl)-4-isopropyl-2(3H)-thiazolone;
5-(4-dimethylaminobenzoyl)-4-methyl-2(3H)-thiazolone;
4-ethyl-5-phenylacetyl-2(3H)-thiazolone;
5-(3-methoxybenzoyl)-2(3H)-thiazolone;

and 5-(3,4-dimethylthio)benzoyl]-4-propyl-2(3H)-thiazolone

The formula 1 compounds can be prepared in any manner by standard techniques analogously known by those skilled in the art. For example the formula 1 compounds can be prepared by a Friedel-Crafts acylation of a thiazolone of formula 3

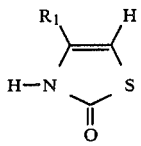

wherein $R_1$ is as defined above. The acylating reagent can be an acid halide of formula 4

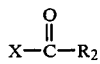

wherein $R_2$ is as defined above and X is a bromo group or preferably a chloro group. In addition the acylating reagent of the Friedel-Crafts reaction can be the free acid or acid anhydride corresponding to the formula 4 acid halide. Mixed acid anhydrides may also be utilized. The Friedel-Crafts reaction is well known by those skilled in the art and has been reviewed by P. H. Gore in "Friedel-Crafts and Related Reactions", G. A. Olah, editor, VOl. III, Part 1, Interscience Publications, New York, 1964.

The Friedel-Crafts reactions of this invention are performed by premixing about 1 molar equivalent of the appropriate thiazolone of formula 3 with about 1 molar equivalent to about 10 molar equivalents, preferably about 3 molar equivalents, of a Lewis acid catalyst in a suitable solvent, for example, petroleum ethers; a chlorinated aromatic, such as 1,2,4-trichlorobenzene or o-dichlorobenzene; carbon disulfide; nitro-benzene or a chlorinated hydrocarbon, such as tetrachloride, ethylene chloride, methylene chloride, chloroform or tetrachlorethane. About 1 molar equivalent to about 10 molar equivalents, preferably about 1.1 molar equivalents of the appropriate acid halide of formula 4 is added, preferably dropwise, to the mixture of thiazolone, Lewis acid, and solvent and the reaction is allowed to proceed for about ½ hour to about 100 hours, preferably from about 1 hour to about 10 hours depending on the reactants, the solvent, and the temperature which can be from about $-78°$ to about 150° C., preferably about 0° to about 100° C., most preferably about 60° C. to 100° C. The resulting aroylthiazolone may be isolated from the reaction mixture by any suitable art-known procedure, such as by quenching the reaction mixture with ice water and subsequently removing the product by filtration or extraction and solvent removal or by acid quenching and collection of the resulting precipatate. Purification can be accomplished by, for example, recrystallization from ethanol.

Lewis acid catalysts suitable for use in the Friedel-Crafts reactions described herein are, for example, a metal, such as aluminum, cerium, copper, iron, molybdenum, tungsten, or zinc; a Bronstead acid, such as a phosphoric acid, sulfuric acid, sulfonic acid, or a hydrohalo acid, such as hydrochloric or hydrobromic acid; halogen substituted acetic acids, such as chloroacetic or trifluoroacetic acids; or a metallic halide, such as a boron halide, zinc chloride, zinc bromide, berryl chloride, copper chloride, iron(III) bromide, iron(III) chloride, mercury(II) chloride, mercury(I) chloride, antimony bromide, antimony chloride, titanium(IV) bromide, titanium(IV) chloride, titanium(III) chloride, aluminum bromide or preferably aluminum chloride.

Alternatively, those formula 1 compounds wherein $R_2$ is a phenyl or benzyl substituted with a $(C_1-C_4)$ alkylthio, amino, mono- or di-alkylamino, pyrrolidino, piperidino, morpholino piperazino or $N-(C_1-C_4)$alkylpiperazino can be prepared from the corresponding formula 1 compound wherein $R_2$ is a fluoro substituted phenyl group by an aromatic electrophilic substitution reaction using conventional techniques. Typically the fluoro substituted compound will be allowed to react with an appropriate thiol or amino substituted at elevated temperatures to effect the desired substitution.

Further the formula 1 compounds wherein $R_2$ is a $(C_1-C_4)$ alkylsulfinyl and $(C_1-C_4)$ alkylsulfonyl substituted phenyl or benzyl group can be prepared from the corresponding formula 1 compound wherein $R_2$ is a $(C_1-C_4)$ alkylthio phenyl or benzyl group by simple selective oxidation. Such oxidations can be performed using hydrogen peroxide or metachloroperbenzoic acid.

The thiazolones of formula 3 are generally available or can be readily prepared by standard laboratory procedures. For example 4-methyl-2(3H)-thiazolone is prepared by reaction of chloroacetone and potassium thiocyanate in aqueous sodium bicarbonate by the procedure of Tcherniac, *J. Chem. Soc.*, 115, 1071 (1919).

The acylating agents of formula 4 are simple derivatives of readily available or preparable benzoic acids and phenylacetic acids. Acid chlorides can be easily prepared from the corresponding carboxylic acids by treatment with thionyl chloride using techniques well known to those skilled in the art.

The compounds of formula 1 are cardiotonic agents useful in the treatment of heart failure. These compounds can also be used in the treatment of any other condition requiring enhanced myocardial contractile force.

The utility of formula 1 compounds as cardiotonics may be determined by administering the test compound (0.1–100 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagentic flow probe may be placed around the root of the ascending aorta for measuring cardiac output less coronary blood flow. Heart failure is induced by administering sodium pentobarbital (20 to 40 mg/kg) followed by a continuous infusion of 0.25-2 mg/kg/min. or propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severly depressed. Reversal of these effects by the test compound indicates cardiotonic activity.

The compounds may be administered in various manners to achieve the desired effect. The compounds may be administered alone or in the form of pharmaceutical preparations to the patient being treated either topically, orally or parenterally, that is, intravenously or intramusuclarly. The amount of compound administered will vary with the patient, the severity of the cardiac failure and the mode of adminstration.

For topical, oral or parenteral administration the cardiotonically effective amount of compound and the amount required to enhance myocardial contractile force is from about 0.1 mg/kg of patients body weight per day up to about 400 mg/kg of patient body weight per day and preferably from about 0.3 mg/kg of patient body weight per day up to about 120 mg/kg of patient body weight per day.

For oral administration a unit dosage may contain, for example, from 5 to 700 mg of the active ingredient, preferably about 15 to 235 mg of the active ingredient. For parenteral administration a unit dosage may contain, for example, from 5 to 700 mg of the active ingredient, preferably about 15 to 210. Repetitive daily administration of the compounds may be desired and will vary with the condition of the patient and the mode of administration.

As used herein, the term "patient" is taken to mean warm blooded animals, for example, birds, such as chickens and turkeys, and mammals, such as sheep, horses, bovine cows and bulls, pigs, dogs, cats, rats, mice, and primates, including humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type contain, for example, lubricants and an inert filler, such as lactose, sucrose, or cornstarch. In another embodiment the compounds of general formula 1 can be tableted with conventional tablet bases such as lactose, sucrose, or cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compounds in a physiologically acceptable diluent with a pharmaceutical carrier which can be a sterile liquid such as water, an alcohol, an oil or other acceptable organic solvent with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, aqueous saline, aqueous dextrose and related sugar solutions, ethanol and glycols such as propylene glycol or polyethylene glycol, or 2-pyrrolidone are preferred liquid carriers, particularly for injectable solutions.

The compounds can be adminstered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic ®, a silicone rubber manufactured by the Dow-Corning Corporation.

The following specific examples further illustrate the preparation and use of the compounds of formula 1 but are not intended to limit the scope of the invention.

EXAMPLE 1

5-(4-Fluorobenzovl)-4-Methyl-2(3H)-Thiazolone

4-Fluorobenzoyl chloride (25.3 g, 0.16 mol) was added dropwise to a mixture of aluminum chloride (60 g, 0.45 mol) and 4-methyl-2(3H)-thiazolone (17.3 g, 0.15 mol) in tetrachloroethane (200 ml). After the addition was complete, the mixture was stirred for 5 hours at 90° C. After the mixture cooled to room temperature, 2N hydrochloric acid (200 ml) was added dropwise. The resulting precipitate was collected, washed with water and then with dichloromethane. The solid was then dissolved in ethanol and heated with charcoal. Subsequent recrystalization from ethanol gave the title compound (18.4 g), M.p. 209°–210° C.

In a like manner but substituting o-chlorobenzoyl chloride, m-trifluoromethyl, or m,p-methylenedioxyphenylacetyl chloride for p-fluorobenzoyl chloride in the above example gives 5-(2-chlorobenzoyl)-4-methyl-2(3H)-thiazolone, 5-[3-(trifluoromethyl)benzoyl]-4-methyl-2(3H)-thiazolone or 5-(3,4-methylenedioxyphenylacetyl)-4-methyl-2(3H)-thiazolone, respectively.

In a like manner but substituting 4-ethyl-2(3H)-thiazolone for 4-methyl-2(3H)-thiazolone in the above example gives 4-ethyl-5-(4-fluorobenzoyl)-2(3H)-thiazolone.

EXAMPLE 2

5-[4-(dimethylamino)benzoyl]-4-methyl-2(3H)-thiazolone

Dimethylamine (100 ml, 40% solution) was added to a solution of 5-(4-fluorobenzoyl)-4-methyl-2(3H)-thiazolone (4.7 g) in ethanol (200 ml). The mixture was stirred in a sealed stainless steel vessel at 120° C. for 16 hours. After cooling to ambient temperature the solvent and excess dimethylamino was evaporated. The residue was recrystallized twice from ethanol to give the title compound, mp. 224°–226° C.

In a like manner but substituting pyrrolidine, morpholene or 1-methylpiperazine for the dimethylamino in the above example gives
5-[4-(pyrrolidinyl)benzoyl]-4-methyl-2(3H)-thiazolone,
5-[4-(morpholinyl)benzoyl]-4-methyl-2(3H)-thiazolone,
or 5-4-(4-methylpiperazinyl)benzoyl]-4-methyl-2(3H)-thiazolone.

EXAMPLE 3

4-Methyl-5-[4-(Methylthio)benzoyl]-2(3H)-Thiazolone

Gaseus methylmercaptan is added to a solution of 5-(4-fluorobenzoyl)-4-methyl-2(3H)-thiazolone (4.7 g) in ethanol (200 ml) to saturation. The mixture is heated at 120° C. in a sealed stainless steel container for 16 hours. After cooling to ambient temperature, the mixture is evaporated to dryness. The residue is recrystallized twice from ethanol to give the title compound.

Substituting 1-butanethiol for methyl mercaptan gives 5-[4-(butylthio)benzoyl]-2(3H)-thiazolone.

EXAMPLE 4

4-Methyl-5-[4-(Methylsulfinyl)benzoyl]-2(3H)Thiazolone

Hydrogen peroxude (1 equivalent, 30%) is added to a solution of 4-methyl-5-[4-(methylthio)benzoyl]-2(3$\underline{H}$)-thiazolone (2.7 g) in glacial acetic acid (80 ml). The mixture is stirred for 3 hours at 50° C. The precipatate obtained on addition of water is recrystallized from ethanol to give the title compound.

Using 2.5 equivalents of hydrogen peroxide and extending the reaction twice to 16 hours at 50° C. gives 4-methyl-5-[4-(methylsulfonyl)benzoyl]-2(3$\underline{H}$)-thiazolone.

EXAMPLE 5

A tablet is prepared from

| | |
|---|---|
| 5-(4-Fluorobenzoyl)-4-methyl-2(3$\underline{H}$)-thiazolone | 250 mg |
| starch | 40 mg |
| talc | 10 mg |
| magnesium stearate | 10 mg |

EXAMPLE 6

A capsule is prepared from

| | |
|---|---|
| 5-(4-dimethylaminobenzoyl)-4-methyl-2(3$\underline{H}$)-thiazolone | 400 mg |
| talc | 40 mg |
| sodium carboxymethylcellulose | 40 mg |
| starch | 120 mg |

We claim:

1. A method of treating heart failure in a patient in need thereof which comprises administering to the patient a cardiotonically effective amount of an aroylthiazolone of the formula

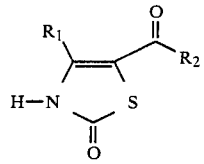

wherein $R_1$ is a hydrogen or ($C_1$-$C_4$)alkyl group; and
$R_2$ is a phenyl or benzyl group optionally substituted with one or two members of the group consisting of ($C_1$-$C_4$) alkyl, ($C_1$-$C_4$)alkoxy, ($C_1$-$C_4$)alkylthio, ($C_1$-$C_4$)alkylsulfinyl, trifluoromethyl, cyano, amino, mono- and di-($C_1$-$C_4$)alkylamino, and halogen.

2. A method of claim 1 wherein $R_1$ is a hydrogen, methyl, or ethyl group.

3. A method of claim 1 wherein $R_2$ is an optionally substituted phenyl group.

4. A method of claim 2 wherein $R_2$ is an optionally substituted phenyl group.

5. A method of claim 1 wherein $R_2$ is a phenyl substituted with an amino or a mono- or di-($C_1$-$C_4$)alkylamino group.

6. A method of claim 2 wherein $R_2$ is a phenyl substituted with an amino or a mono- or di-($C_1$-$C_4$) alkylamino group.

7. A method of claim 1 wherein $R_2$ is a dimethylaminophenyl group.

8. A method of claim 2 wherein $R_2$ is a dimethylaminophenyl group.

9. A method of claim 1 wherein $R_1$ is a methyl group and $R_2$ is a dimethylaminophenyl group.

10. A method of enhancing myocardial contractile force in a patient in need thereof which comprises administering to the patient a therapeutically effective amount of an aroylthiazolone of the formula

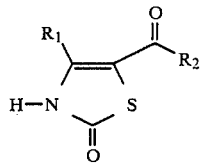

wherein $R_1$ is a hydrogen or ($C_1$-$C_4$)alkyl group; and
$R_2$ is a phenyl or benzyl group optionally substituted with one or two members of the group consisting of ($C_1$-$C_4$) alkyl, ($C_1$-$C_4$)alkoxy, ($C_1$-$C_4$)alkylthio, ($C_1$-$C_4$)alkylsulfinyl, ($C_1$-$C_4$) alkylsulfonyl, trifluoromethyl, cyano, amino, mono- and di-($C_1$-$C_4$) alkylamino, and halogen.

11. A method of claim 10 wherein $R_1$ is a hydrogen, methyl, or ethyl group.

12. A method of claim 10 wherein $R_2$ is an optionally substituted phenyl group.

13. A method of claim 11 wherein $R_2$ is an optionally substituted phenyl group.

14. A method of claim 10 wherein $R_2$ is a phenyl substituted with an amino or a mono- or di-($C_1$-$C_4$) alkylamino group.

15. A method of claim 11 wherein $R_2$ is a phenyl substituted with an amino or a mono- or di-($C_1$-$C_4$) alkylamino group.

16. A method of claim 10 wherein $R_2$ is a dimethylaminophenyl group.

17. A method of claim 11 wherein $R_2$ is a dimethylaminophenyl group.

18. A method of claim 10 wherein $R_1$ is a methyl group and $R_2$ is a dimethylaminophenyl group.

* * * * *